United States Patent [19]
Müller et al.

[11] Patent Number: 5,705,533
[45] Date of Patent: Jan. 6, 1998

[54] 10-THIO-SUBSTITUTED 1,8-DIHYDROXY-9 (10H)-ANTHRACENONE PHARMACEUTICALS

[75] Inventors: Klaus Müller, Regensburg, Germany; Hsu-Shan Huang, Taipei, Taiwan; Wolfgang Wiegrebe, Zeitlarn, Germany

[73] Assignee: Teva Pharmaceutical Industries Ltd., Kiryat Nordau Netanya, Israel

[21] Appl. No.: 487,344

[22] Filed: Jun. 7, 1995

[51] Int. Cl.$^6$ .......... A61K 31/22; A61K 31/135; A61K 31/12

[52] U.S. Cl. .......... 514/656; 514/532; 514/546; 514/569; 514/680; 514/863; 560/10; 560/139; 562/431; 564/427; 568/47

[58] Field of Search .......... 514/532, 569, 514/656, 680, 863; 560/10; 562/431; 564/427; 568/47

[56] References Cited

U.S. PATENT DOCUMENTS 4,997,961  3/1991  Bruce .................. 552/289
5,002,967  3/1991  Mueller et al. .......... 514/473

FOREIGN PATENT DOCUMENTS 0314405  3/1989  European Pat. Off. .

OTHER PUBLICATIONS

Mueller, et al., J. Med. Chem., 37:1660–1669 (1994).

Mueller, et al., J. Med. Chem., 36: 4099–4107 (1993).

d'Ischia, et al., Synthesis, 430–431 (1986) No. 5.

Tanzer, et al., Arch. Pharm., 324: 841–846 (1991).

*Primary Examiner*—Peter O'Sullivan
*Attorney, Agent, or Firm*—Kenyon & Kenyon

[57] ABSTRACT

10-thio-substituted 1,8-dihydroxy-9(10H) anthracenones, therapeutic compositions containing at least one of the 10-thio-substituted 1,8-dihydroxy-9(10H) anthracenones of the invention and methods of treating inflammatory conditions are provided.

18 Claims, No Drawings

10-THIO-SUBSTITUTED 1,8-DIHYDROXY-9 (10H)-ANTHRACENONE PHARMACEUTICALS

FIELD OF THE INVENTION

This invention relates to anthracenone compounds useful in the treatment of allergic and inflammatory conditions and therapeutic compositions containing such compounds. The invention relates also to the provision of therapeutic compositions effective at low dose with low irritancy.

BACKGROUND OF THE INVENTION

Intimation in the body occurs in response to numerous conditions including, but not limited to, physical injury, allergy, tumor growth, certain disease states, chemical damage, and bacterial, parasitic or viral infection. Typically, intimation results in both local and systemic effects. Representative of local effects that can occur are increased vascular permeability, release of degradative enzymes, migration to the affected site by leukocyte cells, neutrophil burst response to destroy invading cells, and the secretion of cytokines. There is considerable interest in the provision of therapeutic compositions containing new compounds that are capable of controlling intimation in the body.

An example of a common inflammatory condition (disease) is psoriasis-a widespread, chronic, inflammatory and scaling skin disease, chiefly characterized by increased cell proliferation to the epidermis. Typically hyperproliferation alone is not sufficient to produce a psoriatic lesion, in that an inflammatory component also plays an important role in the disease process, Fry, L., Br. J. Dermatol., 119, 445–461 (1988).

Psoriasis is known to be associated with numerous biochemical abnormalities. Lowe, N., Drug Der. Res., 13,147–155 (1988). One biochemical characteristic of psoriatic skin is the presence of elevated concentrations of oxygenation products of arachidonic acid. In particular, evidence has been provided showing the enhanced production of lipoxygenase (LO) products, such as leukotriene $B_4$ ($LTB_4$) and 5-hydroxyeicosatetraenoic acid (5-HETE). Additionally, the effects of lipoxygenase (LO) products in the skin correlate with several pathological features of psoriasis, in particular, leukocyte migration to and enhanced cell proliferation at the site.

The activity of several antipsoriatic agents has been correlated with their effects on the 5-lipoxygenase (5-LO) pathway, Ford-Hutchinson, A. W., Lipoxygenases and Their Products 137–160 (1991). In particular, a correlation has been demonstrated between the therapeutic effects of certain antipsoriatic drugs and the effect of these compounds on lipoxygenase enzymes. Accordingly, regulation of lipoxygenase pathways is an important target for therapeutic intervention in the treatment of psoriasis and other inflammatory conditions or allergic conditions. See, for example, Iones, G. H. et al., J. Med. Chem., 29, 1504–1511 (1986) and Venuti, M. C. et al., J. Med. Chem., 31, 2132–2136 (1988). However, in order for a therapeutic treatment to be effective, both the inflammatory and hyperproliferative aspects of the condition must be addressed.

Anthralin (1,8-dihydroxy-9(10H)-anthracenone), also referred to as "dithranol" is probably the most commonly used topical agent for the treatment of psoriasis. However, anthralin therapy causes several unpleasant side effects. For example, non-affected skin surrounding a psoriatic lesion to which anthralin is applied frequently becomes irritated. Additional side effects at the site of application, which are representative of a condition of intimation or irritancy are known to include erythema, inflammatory edema, and elevation in skin temperature.

Substantial evidence suggests that free radicals (Firmen, M. J., Lancet II, 1129–1130 (1984), Shroot, B. et al., Arzneim.-Forsch./Drug Res., 36, 1253–1255 (1986)) and active oxygen species (Muller, K. et al., Arch. Pharm. (Weinheim), 320, 59–66 (1987), Muller, K. and H. Kappus, Biochem. Pharmacol., 37, 4277–4280 (1988), Muller, K. et al., Photochem. Photobiol., 52, 445–450 (1990), Muller, K. et al., Arzneim.-Forsch/Drug Res., 41, 1176–1181 (1991)) play a key role in both the therapeutic activity and side effects of anthralin.

P. G. Unna investigated the minimal structure of several anthracenone derivatives required for therapeutic activity and found that anthralin, as well as 1-hydroxy-9(10H)-anthracenone were effective in the treatment of psoriasis, Dermatol. Wochenschr., 62, 116–137 (1916). The latter compound was stated to be a minimum structure for antipsoriatic activity. Although there have been attempts to develop new therapeutically effective derivatives of anthralin, for which initial reports were promising, later reports have indicated that these compounds were less effective and caused more unpleasant side effects than anthralin itself (Kammerau, B. et al., "Absolute Concentrations of Dithranol and Triacetyl-Dithranol in the Skin Layers After Local Treatment: In Vivo Investigations with Four Different Types of Pharmaceutical Vehicles", J. Invest. Dermatol., 64, 145–149 (1975), and Greaves, M. W., "Irritation and Staining by 10-Butyryl-Dithranol (Butantrone)", Int. J. Clin. Pharm. Res., 6, 315–316 (1986)). For example, butantrone, an anthralin derivative introduced in 1980 by Mustakallio, (Mustakallio, K. K. et al., "1,8-Dihydroxy-10-Acyl-9-Anthrones with Anti-Psoriasis Properties, Finland Patent 57743 (CI C07C49/747)", Chem. Abstr., 1980, 93, P 204348z) is a C-10-butyryl derivative that cannot be cleaved to form anthralin. When applied therapeutically, this compound elicits a widespread and delayed irritation effect in many patients. Additional alkylacyl derivatives are described in published European Patent Specification Number 0 017 420 A1 filed on Mar. 25, 1980 bearing application number 80300928.1.

Additional references which disclose anthralin derivatives having anti-inflammatory (or anti-psoriatic) activity include Tanzer, H. et al., Arch. Pharm., 324, 841–846 (1991); U.S. Pat. No. 4,299,846 to Mustakallio et al.; and numerous U.S. Patents to Schroot et al. (for example, U.S. Pat. Nos. 4,677,123, 4,558,069, 4,464,301, 4,568,743, 4,755,530, 4,826,996, and 4,997,961).

10-substituted 1,8-dihydroxy-9(10H)-anthracenone analogs useful in the treatment of psoriasis have been synthesized in which one or both active methylene protons at C-10 are replaced by suitable substituents which permit control over the release of active oxygen species, Müller, K. et al. (1993). These 10-substituted anthracenone compounds contain arylacyl or phenylalkkylidene moieties at the C-10 position, resulting in enhanced antilipoxygenase activity of the compound. These blocked compounds may further be modified by introducing the phenolic form of the arylacyl or phenylalkylidene substituent.

Other substituted anthralin compounds shown to have anti-psoriasis effect include specific thio-substituted anthralin analogues, (U.S. Pat. No. 4,997,961 to Bruce).

As noted above, psoriasis is typically characterized by both a hyperproliferative component and a common inflammatory component. There is thus a continuing need for effective compounds that address these aspects of psoriasis.

SUMMARY OF THE INVENTION

The present invention is directed to novel 10-thio-substituted 1,8-dihydroxy-9-(10H) anthracenone compounds and analogs thereof, having therapeutic utility with respect to allergic or inflammatory conditions. In particular, many of the improved anthracenone compounds provided for according to the practice of the invention are effective at low concentrations for treatment of patients suffering from allergic or inflammatory conditions. Because these compounds may be administered at low concentrations, the undesirable allergic or inflammatory effects caused, in whole or in part, by free radicals or active oxygen species that are generated by anthracenone compounds are substantially eliminated.

Accordingly, in one embodiment of the invention, there is provided an anthracenone compound according to formula III, as defined below, said compound containing a substituent R, wherein R represents a branched or straight chain alkyl group having from 1 to 4 carbon atoms, said alkyl group being substituted with at least one substituent selected from the group consisting of a carboxyl, carboxyl ester, hydroxyl, sulfhydryl, substituted phenyl, benzyl and substituted benzyl groups or a substituted phenyl group.

In a preferred embodiment of the invention, R represents a substituted phenyl group having at least one substituent selected from the group consisting of methyl ester, amino and sulfhydryl groups. In another preferred embodiment, R represents a straight or branched chain alkyl group having 1 to 4 carbon atoms, said alkyl group having a substituent selected from the group consisting of sulfhydryl and phenyl groups.

Additionally, there are provided compounds which are functional analogs of the compound of formula III compound.

As aforementioned, therapeutic compositions of the invention are effective at doseages that substantially eliminate the adverse inflammatory or irritancy effects normally associated with the use of 1,8-dihydroxy-9(10H)-anthracenone and related compounds. Accordingly, thre is provided a therapeutic composition comprising a therapeutically effective amount of at least one compound of the invention and a pharmaceutically acceptable carrier.

Representative of allergic or inflammatory conditions (diseases) that may be treated according to the practice of the invention are rheumatoid arthritis, osteoarthritis, multiple sclerosis, allergic rhinitis, asthma, psoriasis, eczema, seborrhea, contact dermatitis, sunburn and inflammatory diseases of the digestive tract such as ulcerative colitis. Additionally, the compounds of the invention have anti-proliferative effects and anti-neoplastic effects.

In another aspect of the invention, there is provided a method of treating an allergic or inflammatory condition in a patient in need thereof comprising administrating to said patient a therapeutically effective amount of a composition comprising at least one of the 10-thio-substituted anthracenone compounds of the invention and a pharmaceutically acceptable carrier.

Further additional, representative and preferred aspects of the invention are described below according to the following detailed description of the invention.

DETAILED DESCRIPTION OF THE INVENTION

As set forth above, the compounds of the invention are 10-thio-substituted 1,8-dihydroxy-9(10H)-anthracenones or analogs thereof.

According to the practice of the invention, there are provided 10-thio-substituted 1,8-dihydroxy-9(10H)-anthracenone compounds according to formula III,

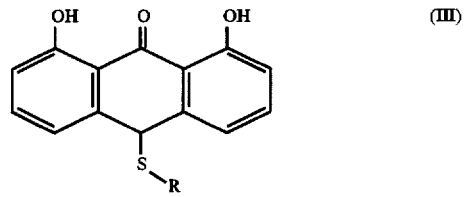

wherein R represents a straight or branched chain alkyl group having 1 to 4 carbon atoms, said alkyl group being substituted with one or more of the groups selected from COOH (or an ester thereof), —OH, —SH, and substituted phenyl and benzyl, or R represents substituted phenyl. Substituents of the phenyl or benzyl group include one or more of the groups —OH, —SH, —NH2, and ester alkyl having 1 to 3 carbon atoms. Preferred compounds according to the practice of the invention include those described in Table I below.

Aerobic life is dependent upon the ability to metabolize chemical compounds oxidatively, for example, using oxygen. Metabolism of oxygen is, however, associated with the unavoidable production of oxygen-derived toxic compounds including radicals and active oxygen species (for example, the oxygen anion radical $O_2^-$, OH -radical, hydrogen peroxide and an excited state species, singlet molecular oxygen. Accordingly, close regulation of the production of such substances, which are toxic to aerobic life, is necessary.

In humans, the controlled release of oxygen-derived free radicals by specialized immune system-related cells performs an antibacterial function. See, for example, Del Maestro, R. F., *Free Radicals in Molecular Biology, Aging, and Disease*, D. Armstrong et al., eds., Raven Press, New York, N.Y., at 87–102 (1984). However, the presence or improper regulation of free radical species is associated with numerous disease states (See, for example, R. F. Del Maestro at page 91 thereof), and free radical-induced injury normally occurs during inflammatory processes. The inflammatory reaction to injury or infection is defined by a wide variety of cellular responses and chemical (biochemical) reactions. The production of free radicals and active oxygen species plays an important role in the creation and maintenance of an inflammatory state. For a review of these phenomena, see for example, Rainsford, K. D. and Swann, B. P., "The Biochemistry and Pharmacology of Oxygen Radical Involvement in Eicosanoid Production" in *The Biology and Chemistry of Active Oxygen*, J. V. Bannister et al., eds., Chapter 5, Elsevier, New York, N.Y. (1984).

The metabolism of arachidonic acid, itself a precursor of many biologically important compounds, including for example, eicosanoids, prostaglandins, leukotrienes ($LTB_4$, $LTC_4$, $LTD_4$, and for example, $LTE_4$) and peptidoleukotrienes, through which an inflammatory condition is mediated, also plays a role in inflammatory responses. The present invention relates in part to the regulation of abnormal arachidonic acid metabolism to thereby provide relief from inflammatory or allergic conditions.

As aforementioned, a principle advantage of the therapeutic compounds of the invention is that they may be administered to a patient at doseage concentration that provides therapeutic effects, including the substantial inhibition of lipoxygenase activity and/or hyperproliferation, and wherein side effects, such as irritancy or inflammation that may be caused by said compounds are minimized so as not to render the therapeutic effects thereof ineffective. In connection herewith it is understood that "patient" includes a human patient, and as expected, a veterinary patient. Also, by "substantial inhibition" is meant the inhibition of the biological activity to a level such that clinical symptoms, such as inflammation are visibly decreased.

Clinical Indications Subject to Treatment According to the Practice of the Invention The following conditions are selected for description herein as being representative of inflammatory, allergic, or neoplastic conditions that are suitable for treatment according to the practice of the invention. Each of these condition involves intimation, hyperproliferation and/or generation of free radicals and active oxygen species.

Arthritic Disease

Rheumatoid arthritis is a chronic inflammatory disease primarily of the joints that may result in permanent loss of joint function. Irreversible loss of joint function is attributed to severe degradation of collagen, bone, ligament and tendon. Associated chronic intimation results, in part, from immune response at the affected joint, although the exact nature of the triggering antigens is unknown. The immune response may be autoimmune in origin. Mullins, D. E. and Rohrlich, S. T. *Biochemica et Biophysica Acta*, 695, 177–214 (1983) at 192–193 describe the etiology of the disease in detail. Briefly, there is a progressive loss of cartilage (a connective tissue) caused by invading cells. Both collagen and proteoglycan components of the cartilage are degraded by enzymes released at the affected site.

Neoplastic Conditions

The therapeutic compositions of the invention may be used in the treatment of a wide variety of cancers such as carcinomas, sarcomas, melanomas and lymphomas, which may affect a wide variety of organs, including, for example, the lungs, mammary tissue, prostate gland, small or large intestine, liver, heart, skin, pancreas and brain. The therapeutic compositions may be administered to patients in the case of treatment of tumors, for example, by injection (intravenously, intralesionally, peritoneally, subcutaneously), or by topical application and the like as would be suggested according to the routine practice of the art.

Psoriasis and Contact Dermatitis

Psoriasis is a widespread, chronic, inflammatory and scaling skin disease. Contact dermatitis, in contrast, is a short term allergic condition characterized by scaling skin. Both psoriasis and contact dermatitis are characterized by increased epidermal cell proliferation at the affected site or sites, i.e. lesion(s).

Therapeutic Compositions and Administration Thereof

The amount of 10-thio-substituted 1,8-dihydroxy-9(10H) anthracenone (or analog thereof) administered to a patient for the prevention or inhibition of an inflammatory or allergic condition, for anti-proliferative or anti-neoplastic effect, can be determined readily for any particular patient according to recognized procedures. Representative of suitable quantities of the compounds of the invention (to be mixed, optionally, with a pharmaceutically acceptable carrier) include, for example, from about 10 to 100 milligrams for oral administration, from about 10 to 100 milligrams for injection, from about 10 to 500 milligrams for a suppository, and from about 0.1% to about 5.0% by weight of a topically applied product such as ointment, cream, gel, aerosol, or liquid. Precise dosing for a patient can be determined according to routine medical practice for each of the particular compounds of the invention taking into consideration the level of therapeutic activity required to treat the condition and the level of any side effects associated with each milligram of active ingredient.

Additional information useful in the selection of therapeutic compositions is provided as follows. For use in the treatment of inflammatory or degenerative conditions, as those terms are recognized in the art, the therapeutic compositions may be administered, for example, by injection at the affected site, by aerosol inhalation (as in the case of emphysema or pneumonia), or by topical application or transdermal absorption as would also be suggested according to the routine practice of the art.

As described above, the 10-thio-substituted-9-anthacenones of the invention (or analogs thereof) may be incorporated into a pharmaceutically-acceptable carrier or carriers for application (directly or indirectly) to the affected area. The nature of the carrier may vary widely and will depend on the intended location of application and other factors well known in the art. Such carriers of anthralin or anthracenone compounds are well known in the art. See, for example, Kammerau, B. et al., *J. Investigative Dermatology*, 64, 145–149 (1975).

For topical administration, the compositions of the present inveniton may be provided in those pharmaceutical forms in which the compound is applied externally by direct contact with the skin surface. Conventional pharmaceutical forms for this purpose include ointments, ungents, tinctures, solutions, creams, lotions, pastes, jellies, sprays, aerosols, bath oils, shampoos, suspensions, micronized powders, and the like, using a pharmaceutically acceptable carrier, such as petrolatum, lanolin, polyethylene glycol or alcohol. These compositions may also contain an additional inert or pharmacologically active adjuvant, such as a binder, filler, diluent, thickening agent, preservative anti-irritant, moisturizer and the like, and combinations thereof. Certain compositions of this invention may preferably include skin penetrating adjuvants such as, for example, dimethyl sulfoxide (DMSO), dimethyl acetamide, and so forth.

The pharmaceutical composition of this invention may be administered enterally, for example, in the form of tablets, granules, gels, capsules, syrups, drinkable suspensions, or ingestible powders, for example.

The pharmaceutical composition may also be formulated as a suspension or solution and injected, either intravenously, intramuscularly, intradermally, intra- or periolesionally, or subcutaneously using, for example, sterile saline as carrier.

The pharmaceutical composition may also be applied rectally in the form of a suppository, or sublingually, transdermally, and so forth.

Additionally, a compound of the invention may be encapsulated by liposomes and combined with an appropriate pharmaceutical carrier to enhance the incorporation of the resulting composition into the intestinal lumen. Methods of encapsulation in liposomes are known in the art.

If desired, the therapeutic composition of the invention may be incorporated into a bandage or other wound dressing to provide continuous exposure of the wound to the therapeutic compound or compounds. Aerosol applications of the invention composion are also useful. Additionally, the composition may be applied topically to the affected area, typically in the form of a cream, ointment or lotion to the skin. On the skin, it is desirable to continually maintain the treatment composition on the affected area during healing, with several applications of the treatment composition per day being preferred.

Treatment of a patient with a composition of the invention is carried out for a period of time required to prevent, reverse or alleviate the symptoms of the medical condition being treated. The treatment regimen will vary depending on such factors as the particular condition being treated, route of administration of the composition, severity of symptoms, etc. For example, for treatment of psoriasis or contact dermititus by topical administration, a composition containing an amount of about 0.1% to about 5% of a 10-thio-substituted 1,8-dihydroxy-9(10H)anthracenone compound of the invention as active ingredient is applied to the lesion or lesions at least once per day until the symptoms are visually eliminated. Similarly, treatment of allergies is continued until the symptoms, e.g. intimation, itching, etc. are alleviated or until the agent or condition responsible for the allergic response has been removed.

Preparation of the Compounds of Invention

The 10-thio-substituted 1,8-dihydroxy-9(10H)-anthracenones (III) may be prepared according to reaction scheme (I) below. The treatment of anthralin (I) with bromine provided 10-bromo-1,8-dihydroxy-9(10H)-anthracenone (II).[1] In contrast to earlier reports,[2,3] the desired compounds were obtained directly from the intermediate 2 by nucleophilic substitution at C-10 with 1.5–2 equivalents of appropriate mercaptanes.

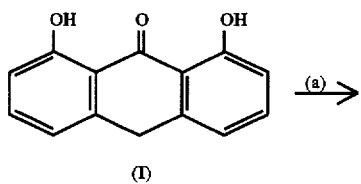

(I)

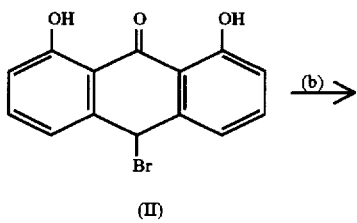

(II)

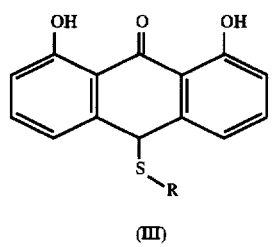

(III)

$^a$R is defined in Table 1. Reagents: (a) $Br_2$, $CS_2$, 50° C.; (b) R—SH, TFA, $CH_2Cl_2$, room temperature.

Specific methods for the preparation of several compounds according to the present invention are described below in Example 4 and the structure of each of the synthesized compounds is confirmed by $^1$H-NMR spectometry, as shown in Example 5.

Biological Data

TABLE 1

5-LO Inhibiton in Bovine PMNL and Antiproliferatve Activity of 10-Thio-Substituted 1,8-Dihydroxy-9(10H)anthracenone Compounds of the Invention

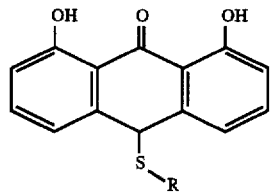

| compd | R | formula$^a$ | mp (°C.) | 5-LO IC$_{50}$ (µM) | AA IC$_{50}$ (µM) |
|---|---|---|---|---|---|
| 3a | $CH_2CO_2C_4H_9$ | $C_{20}H_{20}O_5S$ | 90–91 | 30 (8) | 2.10 |
| 3b | $CH(CH_3)COOH$ | $C_{17}H_{14}O_5S$ | 168–169 | 30 (28) | 0.2 |
| 3c | $CH_2CH_2CO_2CH_3$ | $C_{18}H_{16}O_5S$ | 88–89 | 15 | 1.10 |
| 3d | $CH_2CH_2CO_2C_2H_5$ | $C_{19}H_{18}O_5S$ | 86–87 | 30 (30) | 1.60 |
| 3e | $CH_2CH_2CO_2C_4H_9$ | $C_{21}H_{22}O_5S$ | 72–73 | 30 (62) | 2.30 |
| 3f | $CH_2CH_2CH_2SH$ | $C_{17}H_{16}O_3S_2$ | 58–59 | 30 (14) | 0.77 |
| 3g | $CH(CH_3)CH(CH_3)SH$ | $C_{18}H_{18}O_3S_2$ | 105–106 | | |
| 3h | $CH_2(CHOH)_2CH_2SH$ | $C_{18}H_{18}O_5S_2$ | | | |
| 3i | $2\text{-}CH_3OC_6H_4$ | $C_{21}H_{16}O_4S$ | 135 | 6.3 | 4.25 |
| 3j | $3\text{-}CH_3OC_6H_4$ | $C_{21}H_{16}O_4S$ | 96–97 | 30 (100) | 1.80 |
| 3k | $4\text{-}CH_3OC_6H_4$ | $C_{21}H_{16}O_4S$ | 143–144 | 3.2 | 1.69 |
| 3l | $2\text{-}H_2NC_6H_4$ | $C_{20}H_{15}NO_3S$ | 132–133 | 2.4 | 0.10 |
| 3m | $3\text{-}H_2NC_6H_4$ | $C_{20}H_{15}NO_3S$ | 150$^b$ | 2.4 | 1.90 |
| 3n | $4\text{-}H_2NC_6H_4$ | $C_{20}H_{15}NO_3S$ | 160–161 | 7.5 | 0.90 |
| 4a | $2\text{-}HOC_6H_4$ | $C_{20}H_{14}O_4S$ | 151–152 | 5 | 1.75 |
| 4b | $4\text{-}HOC_6H_4$ | $C_{20}H_{14}O_4S$ | 189–190 | 2.4 | <0.1 |
| 4c | $2\text{-}HSC_6H_4$ | $C_{20}H_{14}O_3S_2$ | 138 | | 0.10 |
| 4d | $3\text{-}HSC_6H_4$ | $C_{20}H_{14}O_3S_2$ | >170 | | >5.0 |
| anthralin | | $C_{14}H_{10}O_3$ | 169–171 | 37 | 0.60 |

TABLE 2

5-LO Inhibiton in Bovine PMNL and Antiproliferatve Activity of 10-Thio-Substituted 1,8-Dihydroxy-9(10H)anthracenone Compounds of the Invention

| Comparative Compound | R | formula[a] | mp (°C.) | 5-LO IC$_{50}$ (µM)[c] | AA IC$_{50}$ (µM)[d] |
|---|---|---|---|---|---|
| 3-A[6] | CH$_2$CO$_2$CH$_3$ | C$_{17}$H$_{14}$O$_5$S | 130–131 | 13 | 190 |
| 3-B[6] | CH$_2$CO$_2$C$_2$H$_5$ | C$_{18}$H$_{16}$O$_5$S | 92–93 | 30(42) | 4.52 |
| 3C[3] | CH$_2$CH(NH$_2$)COOH | C$_{17}$H$_{15}$NO$_5$ | 176–178 | 30(17) | >5 |
| 4A[3] | CH$_2$C$_6$H$_5$ | C$_{21}$H$_{16}$O$_3$S | 155–156 | 30(46) | 1.40 |

[a]All new compounds displayed $^1$H-NMR, FTIR, UV and MS spectra consistent with the assigned structure.
[b]Decomposition.
[c]Inhibition of 5-HETE and LTB$_4$ biosynthesis in bovine PMNL; N = 3 or more, inhibition was significantly different with respect to control, P < 0.01; values in parentheses are percent inhibition at the indicated concentrations (µM), standard errors average 10% of the indicated values.
[d]Antiproliferative activity against HaCaT cells. Inhibition of cell growth was significantly different with respect to that of the control, N = 3, P < 0.01.

EXAMPLES

The following examples are representative of the practice of the invention.

Example 1

Application of Anthracenones to Arthritis-Affected Tissues

Animal model systems are available for studying arthritic disease states in vivo: For example, it has been demonstrated that Wistar rats, when immunized with native type II collagen (isolated from fetal bovine articular cartilage), develop arthritic disease as a result of collagen-immunity response. Such response is believed to be related to the progression of human rheumatoid arthritis. See Smart, J. M. et al. *J. Exp. Med.*, 155, 1–16 (1982) and references cited therein. Other animal models include use of intradermal injection with complete Freunds adjuvant (see Chang et al. *Arth. Rheum.*, 23, 62–71 (1980)) and intraperitoneal injection of Streptococcus cell wall extracts in Lewis rats (see Wilder, et al. *Arth. Rheum.*, 25, 1064 (1982)).

The results of animal studies and the discoveries of the present invention suggest that progression of arthritic disease in humans may be halted, or in fact reversed, using subcutaneous or intraarticular injections of at least one compound of the invention, at a doseage of up to about 5 µg/ml or higher using an injection volume compatible with the volume of the affected site, for example, about 0.1 ml of the therapeutic composition per 10 ml of inflamed synovial fluid, said administration being made on a daily basis for a period of about 1 to about 30 days.

It is expected that improvement will be demonstrated within this period following such daily administrations at which time the injections may be discontinued. If further healing does not occur, a second course of administrations would be indicated and treatment continued until symptoms abate or are eliminated.

Example 2

Bovine PMNL 5-Lipoxygenase Assay

Polymorphonuclear leukocytes (PMNL) were prepared from sodium EDTA-anticoagulated bovine blood, essentially as described by Walstra, P. et al., "Leukotriene Formation by Bovine Polymorphonuclear Leukocytes", *Biochim. Biophys. Acta*, 795,499–503 (1984). Contaminating platelets were removed by repeated centrifugations at 100 g for 20 min. The purified PMN leukocytes were suspended at a concentration of 1×10$^7$ cells/ml in phosphate buffered saline (PBS, composed of 8.00 g NaCl, 0.20 g KCl, 1.00 g Na$_2$HPO$_4$·2H$_2$O, 0.15 g NaH$_2$PO$_4$·H$_2$O, 0.20 g KH$_2$PO$_4$, adjusted to pH 7.4 with 3 N NH$_3$ in a final volume of 1000 ml of double distilled H$_2$O). Cell counts were conducted with a Sysmex microcellcounter CC-130. Preincubation was performed with 2.4 ml of the suspension and 10 µl of a DMSO stock solution of each test compound at the desired concentration in PBS or vehicle control (DMSO at final concentration of 0.4%) for 15 min at 37° C. in a shaking water bath. The syntheses of LTB 4 and 5-HETE were stimulated by the addition of CaCl$_2$ and Ca-ionophore A23187 (final concentrations 2 mM and 20 µM, respectively), and the incubation was conducted for 10 min at 37° C. 5-LO product formation was terminated by the addition of 3.0 ml of methanol/acetonitrile (1+1) containing NDGA as radical scavenger (final concentration 0.01 mM) and prostaglandin B$_2$P$_G$B$_2$ as chromatographic marker (final concentration 0.3 µM). The incubation mixture was kept in an ice bath for 20 min and then centrifuged at 4000 g for 5 min at 0° C. The supernatant was diluted with 5 ml of water and passed through a prewashed (10 ml of methanol and 5 ml of water, sequentially) octadecylsilane reversed phase cartridge (Baker). The eicosanoids were eluted with 3 ml of methanol, diluted with 3 ml of water and subjected to reversed phase high performance liquid chrometography (HPLC) analysis, performed on a 250×4 mm column packed with Nucleosil C$_{18}$ (7 µm particles; Bischoff, Leonberg, Germany). The isocratic elution conditions of LTB$_4$were tetrahydrofuran (THF)/methanol/water/acetic acid (25+30+45+0.1), adjusted to pH 5.5 with concentrated NH$_3$, at a flow rate of 0.9 ml/min (Kontron 420 pump), monitored at 280 nm with a Kontron 735 LC UV detector, whereas 5-HETE was monitored at 232 nm using methanol/water/acetic acid (77+23+0.1), pH 5.5,flow rate 1.0ml/min. Data were recorded on a MacLab data acquisition system (WissTech, Germany) and analysis was performed with the application Peaks on an Apple Macintosh Quadra 700 computer. Integrated areas of the peaks were compared to the PGB$_2$ internal standard and to external standards of test samples. Molar absorption coefficients of Samuelsson et al., Borgeat, P. and B. Samuelsson, "Arachidonic Acid Metabolism in Polymorphonuclear Leukocytes: Effects of Ionophore A23187", *Proc. Nat. Acad. Sci. USA*, 76, 2148–2152 (1979), were used for calculations. Inhibition was calculated by comparison of the mean values of test compound (n=3) with control (n=6–8) activity: (1-test compound/control)×100. Inhibition was statistically significant compared to that of the control (Student's t-test: p<0.05). Each IC$_{50}$ value was derived by interpolation of a log dose vs response plot using four or more concentrations of the compound, spanning the 50% inhibition point.

By the above method, the anthracenone derivatives of the invention were evaluated for their ability to inhibit the production of LTB$_4$ and 5-HETE in isolated bovine polymorphonuclear leucocytes (PMNL), see Walstra, P. et al., "Leukotriene Formation by Bovine Polymorphonuclear Leukocytes", *Biochim. Biophys. Acta*, 795,499–503 (1984); Dannhardt, G. and also M. Lehr, "In-Vitro Evaluation of 5-Lipoxygenase and Cyclo-Oxygenase Inhibitors Using Bovine Neutrophils and Platelets and HPLC", *J. Pharm. Pharmacol.*, 44, 419–424 (1992). LTB$_4$ and 5-HETE concentrations were measured by reversed-phase HPLC with UV detection. Table I summarizes the inhibitory potencies of the compounds of the invention as expressed by their $IC_{50}$ values. The effect of anthralin itself on arachidonic acid lipoxygenation has previously been reported. In human neutrophils and in bovine neutrophils anthralin inhibits the production of $LTB_4$ with an $IC_{50}$ value of 7–74 μM (depending on cell density) and 37 μM, respectively, Schroder, J. -M., "Anthralin (1,8-Dihydroxyanthrone) is a Potent Inhibitor of Leukotriene Production and $LTB_4$-ωOxidation by Human Neutrophils", *J. Invest. Dermatol.*, 87, 624–629 (1986); Tanzer, H. et al., "Anthralin Derivatives—Inhibition of 5-Lipoxygenase—Antipsoriatic Efficacy", *Arch. Pharm. (Weinheim)*, 324, 841–846 (1991). Several compounds of the invention showed 100% inhibition at a concentration of 30 μM and one compounds, compound 31 and 4b (Table 1), had a 5-LO $IC_{50}$ of 2.4 μM.

The results obtained with representative compounds of the invention are shown in Table I.

Example 3

Antiproliferative Activity Assay

HaCaT cells, a rapidly multiplying human keratinocyte cell line, were grown in Dulbecco's modified Eagle medium (DMEM), No. 041-11965A, Gibco) supplemented with 10% fetal calf serum, penicillin (100U/ml), streptomycin (100 μg/ml) in a humidified incubator containing 8% $CO_2$ at 37° C. Cells ($2.5\times10^7$/1.1 ml suspension per well) were seeded on 24-wells-multidishes and grown in DMEM. After 24 hours growth the medium was replaced with fresh medium and the test compounds (0.1–5 μM) were added. Stock solutions of the test compounds were prepared in DMSO and diluted with DMEM to give a final concentration of DMSO of 0.2%. Controls were performed with DMSO or with medium alone. Forty-eight hours after addition of the test compound to the culture, the medium was removed and each well was rinsed with 100 μL PBS. The cells were then incubated with sterile 0.5% trypsin, 0.2% EDTA in PBS for 20 minutes at 37° C. The detached cells from each well were suspended in DMEM and dispersed into single cells by gentle pipetting through an Eppendorf pipette, and cell growth was determined directly by counting the keratinocytes in a Neubauer counting chamber using phase contrast microscopy. Inhibition was calculated by comparison of the mean values of the test compound (N=3) with the control (N=6–8) activity: (1-test compound/control)×100. Inhibition was statistically significant compared to that of control (Student's t-test; P-0.05). Each $IC_{50}$ value was derived by interpolation of a log inhibitor concentration versus response plot using four or more different concentrations of the compound, spanning the 50% inhibition point. Several compounds of the invention had an anti-proliferative $IC_{50}$ value of less than 2 μM. In particular, compounds 31, 4b and 4c had an $IC_{50}$ value of 0.1 μM or less (compound 4b). In addition, each of compounds 31 and 4b showed an $IC_{50}$ value of 2.4/L in the 5-LO inhibition assay (Example 2).

The results of this assay are provided in Table I.

Example 4

Methods of Synthesis

There are hereafter provided processes by which the 10-thio-substituted anthracenone compounds described in Table I were produced. Such procedures, and procedures adapted therefrom, will allow one skilled in the art to prepare similar compounds of the invention.

A general procedure for the synthesis of 10-thio-substituted 1,8-dihydroxy-9(10H)-anthraceneones follows. To a solution of 10-bromo-1,8-dihydroxy-9(10H)-anthracenone [1](1 mmol) and 0.1 mL of trifluoroacetic acid in dry $CH_2Cl_2$ (20 mL) was added dropwise a solution of an appropriate mercaptane (2 mmol) in dry $CH_2Cl_2$ (10 mL) under $N_2$. The reaction mixture was stirred at room temperature for 6 hours. The solvent was removed and the residue purified by chromatography. This procedure was used to synthesize each of the compounds in Table I.

Example 5

Structural Confirmation 1,8-Dihydroxy-10-[(4-hydroxyphenyl)thio]-9(10H)-anthracenone 1,8-dihydroxy-10-[(4-hydroxyphenyl)thio]-9(10H)-anthracenone was synthesized as in Example 4 and analyzed by 1H-NMR: (250 MHz, $CDCl_3$)δ 11.83 (s, 2H), 7.49 (t, 2H, J=8.0Hz), 7.01 (d, 2H, I=7.5 Hz), 6.87 (d, 2H J=8.4 Hz), 6.55 (s, 4H), 5.35 (s, 1H), 4.91 (s, 1H); FTR 3436 (OH), 1630 $cm^{-1}$ (CO); MS m/z 350 (11), 250 (21), 227 (14), 226 (83), 225 (100), 198 (28), 197 (77). Anal. ($C_{20}H_{14}O_4S$); C, H.

Example 6

Additional Experimental Details

Additional information applicable to confirming the results of the synthesis procedures of the invention is as follows.

All temperatures are provided in degrees centigrade. Melting points were determined with a Büchi 510 melting point apparatus and are uncorrected. Chromatography refers to column chromatography using silica gel (E. Merck, 70–230 mesh). $^1$H-NMR spectra were recorded with a Bruker Spectrospin WM 250 (250 MHz); δ values are in ppm relative to a tetramethylsilane internal standard. Fourier-transform-IR spectra (KBr) were recorded on a Nicolet 510M FTIR spectrometer. Mass spectra (EI, 70 eV, unless otherwise stated) were obtained on a Varian MAT CH5, PI-FDMS on a Varian MAT 95.

References (1) Schultz, O. E.; Schultze-Mosgau, H. H. Die Substitution des 1,8-Dihydroxyanthrons-9 in meso-(10)-Stellung. X. Mitt. über L:avcarmen. *Arch. Pharm.* (Weinheim, Ger.) 1965, 298, 273–281.

(2) d'Ischia, M.; Privitera, A.; Prom, G. Interaction of anthralin with cysteine: a new entry into the chemistry of biologically active anthrones. *Tetrahedron Lett.* 1984, 25, 4837 4840.

(3) d'Ischia, M.; Prom, G. Synthesis of 10-alkylthio- and arylthio-1,8-dihydroxy-9-anthrones, a new class of anthracene derivatives of potential pharmacological interest. *Synthesis* 1986, 43g431.

(4) Müller, K.; Gurster, D.; Piwek, S.; Wiegrebe, W. Antipsoriatic anthrones with modulated redox properties. 1. Novel 10-substituted 1,8-dihydroxy-9(10H) anthracenones as inhibitors of 5-lipoxygenase. *J. Med. Chem.* 1993, 36, 40994107.

(5) Müller, K.; Leukel, P.; Ziereis, K.; Gawlik, I. Antipsoriatic anthrones with modulated redox properties. 2.

Novel derivatives of chrysarobin and isochrysarobin -antiproliferative activity and 5-lipoxygenase inhibition. *J. Med. Chem.* 1994, 37, 166>1669.

(6) Brace, J. M. Thio-containing anthralin analogs for the treatment of psoriasis, and their preparation, pharmaceutical compositions, and use. Eur. Pat. Appl. EP 314,405. *Chem. Abstr.* 1989, 111, 173808h.

[several other references need to be included from above]

We claim:

1. A compound according to formula III

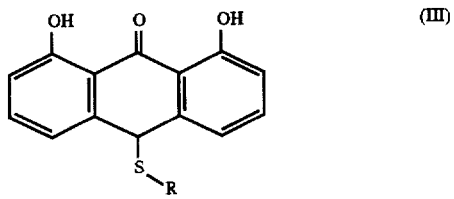

wherein R represents a substituted phenyl group having at least one substituent selected from the group consisting of methyl ester, amino, hydroxyl and sulfhydryl groups.

2. The compound according to claim 1 wherein R represents a substituted phenyl group selected from the group consisting of $2-H_2NC_6H_4$, $3-H_2NC_6H_4$, $4-H_2NC_6H_4$, $4-HOC_6H_4$, $2-HOC_6H_4$, $2-HSC_6H_4$, $3-HSC_6H_4$, $4-CH_3OC_6H_4$, $3-CH_3OC_6H_4$ and $2-CH_3OC_6H_4$.

3. The compound according to claim 1 wherein R represents a substituted phenyl group selected from the group consisting of $4-HOC_6H_4$, $4-H_2NC_6H_4$, $3-H_2NC_6H_4$ and $2-H_2NC_6H_4$.

4. A therapeutic composition comprising a therapeutically effective amount of at least compound according to claim 2 and a pharmaceutically acceptable carrier.

5. A therapeutic composition comprising a therapeutically effective amount of at least one compound according to claim 3 and a pharmaceutically acceptable carrier.

6. A therapeutic composition comprising a therapeutically effective amount of at least one compound according to claim 1 and a pharmaceutically acceptable carrier.

7. A method for inhibiting or treating an allergic or inflammatory condition in a patient in need thereof comprising administering to said patient a therapeutically effective amount of the composition according to claim 4.

8. A method for inhibiting or treating an allergic or inflammatory condition in a patient in need thereof comprising administering to said patient a therapeutically effective amount of the composition according to claim 5.

9. A method for inhibiting or treating an allergic or inflammatory condition in a patient in need thereof comprising administering to said patient a therapeutically effective amount of the composition according to claim 6.

10. The method according to claim 8 wherein the composition is administered to a patient suffering from psoriasis.

11. The method according to claim 9 wherein the composition is administered to a patient suffering from psoriasis.

12. The method according to claim 8 wherein the composition is administered to a patient suffering from contact dermititis.

13. The method according to claim 9 wherein the composition is administered to a patient suffering from contact dermatitis.

14. The method according to claim 8 wherein the composition is topically applied to an affected area of said patient.

15. The method according to claim 9 wherein the composition is topically applied to an affected area of said patient.

16. The method according to claim 7 wherein the composition is administered to a patient suffering from psoriasis.

17. The method according to claim 7 wherein the composition is administered to a patient suffering from contact dermatitis.

18. The method according to claim 7 wherein the composition is topically applied to an affected area.

* * * * *